US006749736B1

United States Patent
Fuhr et al.

(10) Patent No.: US 6,749,736 B1
(45) Date of Patent: Jun. 15, 2004

(54) ELECTRODE ARRANGEMENT FOR THE DIELECTROPHORETIC DIVERSION OF PARTICLES

(75) Inventors: Günter Fuhr, Berlin (DE); Thomas Schnelle, Berlin (DE); Rolf Hagedorn, Berlin (DE); Torsten Müller, Berlin (DE)

(73) Assignee: Evotec Technologies GmbH (DE)

( * ) Notice: Subject to any disclaimer, the term of this patent is extended or adjusted under 35 U.S.C. 154(b) by 0 days.

(21) Appl. No.: 09/720,222

(22) PCT Filed: Jun. 28, 1999

(86) PCT No.: PCT/EP99/04469
§ 371 (c)(1),
(2), (4) Date: Feb. 22, 2001

(87) PCT Pub. No.: WO00/00292
PCT Pub. Date: Jan. 6, 2000

(30) Foreign Application Priority Data

| Jun. 26, 1998 | (DE) | ............................................. | 198 28 626 |
| Jun. 29, 1998 | (DE) | ............................................. | 198 28 919 |
| Nov. 20, 1998 | (DE) | ............................................. | 198 53 658 |
| Dec. 23, 1998 | (DE) | ............................................. | 198 60 117 |

(51) Int. Cl.⁷ ............................................. G01N 27/453
(52) U.S. Cl. ...................................... 204/643; 204/600
(58) Field of Search .................. 422/72; 210/695; 204/547, 660, 643, 450, 600; 436/45

(56) References Cited

U.S. PATENT DOCUMENTS

| 4,134,744 A | 1/1979 | Peterson et al. ............... 55/118 |
| 4,726,904 A | 2/1988 | Ayers ........................ 210/658 |
| 5,565,105 A | 10/1996 | Thakor ........................ 210/695 |
| 5,569,367 A | * 10/1996 | Betts et al. ................. 204/547 |
| 5,993,630 A | * 11/1999 | Becker et al. ............... 204/547 |

FOREIGN PATENT DOCUMENTS

| WO | 9416821 | 4/1994 | |
| WO | 9804355 | 2/1998 | |
| WO | 98/10869 A1 | * 3/1998 | ............. B03C/5/02 |

OTHER PUBLICATIONS

"Dielectrophoretic Sorting of Particles and Cells in a Microsystem" by Fiedler et al. (XP–000755524) Analytical Chemistry, vol. 70, No. 9, May 1, 1998, pp. 1909–1915.

"Radio–Frequency Microtools for Particle and Live Cell Manipulation" by Fuhr et al.; (Natur Wissenschaftenaufsatze 81, 528–535 (1994). Dec., 1994.

"The LabCD™: A Centrifuge–Based Microfluidic Platform for Diagnostics" by Madou et al. SPIE vol. 3259, 0277–786X/98; pp. 80–93. Apr., 1998.

* cited by examiner

Primary Examiner—Alex Noguerola
(74) Attorney, Agent, or Firm—Baker Botts LLP

(57) ABSTRACT

Electrode arrangement (10) in a microsystem adapted for dielectrophoretic manipulation of particles (30) in a suspension fluid in a channel (21), wherein at least one electrode (11, 11a, 11b, 12) is arranged on a lateral wall of the channel (21), the electrode (11, 11a, 11b, 12) consisting of a plurality of electrode segments adapted to generate at least one field gradient for influencing the movement paths of the particles (30) in the channel (21). In one embodiment of the invention, the particles are moved in the microsystem by exposure to centrifugal and/or gravitational forces.

7 Claims, 14 Drawing Sheets

ELECTRODE ARRANGEMENT FOR THE DIELECTROPHORETIC DIVERSION OF PARTICLES

This application claims priority under 35 U.S.C. 371 from PCT/EP99/04469, Jun. 28, 1999.

BACKGROUND OF THE INVENTION

The invention relates to microsystems adapted to handle suspended particles or biological cells, in particular ot the configuration of electrodes for dielectrophoretic deflection of particles or cells, and applications of such microsystems.

Known in the art is to manipulate fluid-suspended particles in microsystems with electrode-channel-arrangements based upon negative or positive dielectrophoresis, wherein polarization forces are generated during exposure to high-frequency electrical fields, enabling a repulsion from the electrodes and, in conjunction with flow forces in the suspension fluid, making it possible to manipulate the particles in the microsystem. An overview of known microsystem is given e.g. by G. Fuhr et al. in "Naturwissenschaften", Volume 81, 1994, p. 528.

Conventional microsystems have disadvantages relating to the stability and life time of the electrodes, and a limitation to specific potential forms corresponding to the respective electrode geometry.

The microelectrodes of conventional microsystems generally exhibit straight bands, which are oriented in a certain way relative to the channel to achieve specific field barriers in the channel of a microsystem. Mechanical stresses, material fatigue, or production defects can lead to breaks in the straight electrode bands, and hence cause a malfunction of the entire microsystem. In addition, a conventional system is limited to a specific function corresponding to the given electrode structure. Variable actions for particle deflection in a given microsystem are not possible.

A microsystem for dielectrophoretic sorting of particles and cells is known from the publication of S. Fiedler et al. in "Anal. Chem." vol. 70, 1998, p. 1909. The microsystem contains an electrode arrangement with a plurality of strip shaped, triangular or rectangular electrodes.

Consideration is now being given to ways of improving electrode arrangements for microsystems with dielectrophoretic particle deflection to overcome the disadvantages of conventional microsystems. Attention is also directed towards indentifying or developing applications for the improved electrode arrangements.

SUMMARY OF THE INVENTION

In accordance with the present invention, provides a new microsystem adapted for the dielectrophoretic manipulation of particles in a suspension fluid in a channel. The microsystem contains an electrode arrangement with at least one electrode arranged on a lateral wall of the channel. The electrode has plurality of electrode segments facing the channel for generating field gradients. The electrode segments are formed by portions or areas of a metal coating which are exposed to the channel through recesses in an insulating layer that coats the metal coating.

The basic idea underlying the invention is, with an electrode arrangement of a microsystem with dielectrophoretic particle deflection consisting of at least one electrode, to divide the electrode into electrode segments. The electrode segments are set up to be exposed to potentials jointly or separately and, working together, to generate a field barrier corresponding to the function of the respective electrode in the microsystem. The electrode segments are electrode surfaces exposed relative to a fluid in the microsystem, which surfaces are electrically connected as a function of application, wherein the areas of the electrical connections are not exposed relative to the fluid in the microsystem, i.e., are covered or electrically isolated from each other. The transition from conventional, planar-shaped or band electrodes to the electrode segments according to the invention advantageously solves the above object from a variety of standpoints. On the one hand, the electrode segments are less susceptible to faults, as will be explained in detail below. On the other hand, with separate actuation, they permit a multiple functionality of the microelectrodes, and hence of the microsystems themselves, that is not provided in conventional microsystems.

In a first embodiment, the electrode segments are formed by electrodes with a planar or band expansion carrying an insulation layer, which has recesses in predetermined sections. The recesses exhibit the shape and position of the desired electrode segments. Through the recesses, the fluid in the microsystem contacts the electrode, which only becomes active via the recesses or electrode segments due to the insulating or dielectric cover, and is otherwise inactive. This configuration is advantageous for the life time of the electrodes, since even a break off of the entire electrode part open to the fluid will not cause the electrode to fail.

In a second embodiment of the invention, the electrode segments are individually actuatable, independently from each other. The electrode segments that together assume an electrode function are arranged in the microsystem, e.g., along a channel wall, in an area shaped like a conventional electrode that would be provided for performing this function. The electrode segments can be separately exposed to potentials that vary by application relative to the phase position and amplitudes.

In another embodiment of the invention, electrode segments electrically isolated from each other and individually actuatable are arranged as an electrode array. An electrode array consists of numerous point or planar electrode segments, arranged e.g. like a matrix in rows and columns or in other geometric configurations depending on application, of which a predetermined number of electrode segments are exposed with electrical potentials to produce a specific electrode function during the operation of the microsystem, while the remaining electrode segments of the electrode array are not actuated. This is a particularly advantageous configuration of an electrode arrangement according to the invention, since the electrode segments can be differently actuated depending on application, and hence the electrode function can be freely selected. As will be explained below, this function selection can take place irreversibly or reversibly.

Other important aspects of the invention include the geometric configuration of electrode segments, with which gradients, and hence varyingly strong forces can be generated, and/or which are adjusted to the flow profile in the suspension fluid. The advantage to the latter configuration is that the electrodes can be shorter in design, and are exposed to lower forces, while still exhibiting the identical effectiveness as conventional microelectrodes.

Preferred applications of the invention lie in techniques in fluid microsystems for separating, manipulating, charging, fusing, permeating, pairing and aggregating microscopically small, suspended particles (synthetic particles and/or biological particles, e.g., biological cells, cell constituents or macromolecules).

In a special embodiment of the invention, the particles are moved in a microsystem with electrode forms designed conventionally or in accordance with the invention during exposure to centrifugal and/or gravitational forces.

Further features of the invention, its nature and various advantages will become more apparent from the accompanying drawings and the following detailed description.

DETAILED DESCRIPTION

Figure 1:
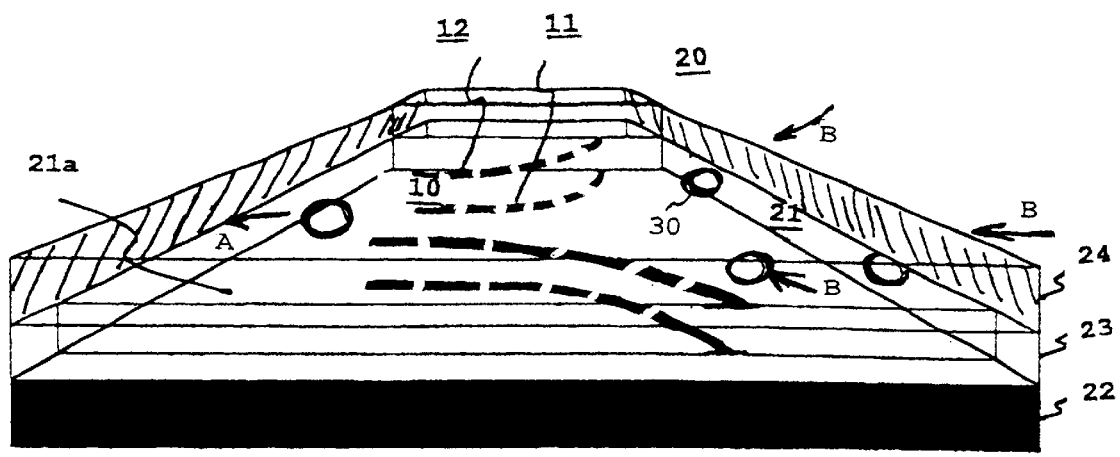
FIG. 1 is a diagrammatic perspective view of a channel structure with microelectrodes for generating force barriers in a micro-channel.

FIG. 1 shows a diagrammatic view of the layout of microelectrodes for generating force barriers in microchannels. The fluidic microsystem 20 is sectionally shown in a hyperperspective side view of a channel structure. The channel 21 is formed by two spacers 23 arranged a distance from each other on a substrate 22, which carry a cover part 24. Such structures are manufactured with known processing techniques in semiconductor technology, for example. The substrate 22 forms the bottom 21a of the channel 21. Correspondingly, the covered surface 21b (not highlighted separately for reasons of clarity) is formed by the cover part 24. The electrode arrangement 10 consists of microelectrodes 11, 12 applied to the bottom 21a or cover surface 21b. Each of the microelectrodes 11, 12 consists of several electrode segments to be described in greater detail below.

Figure 6:
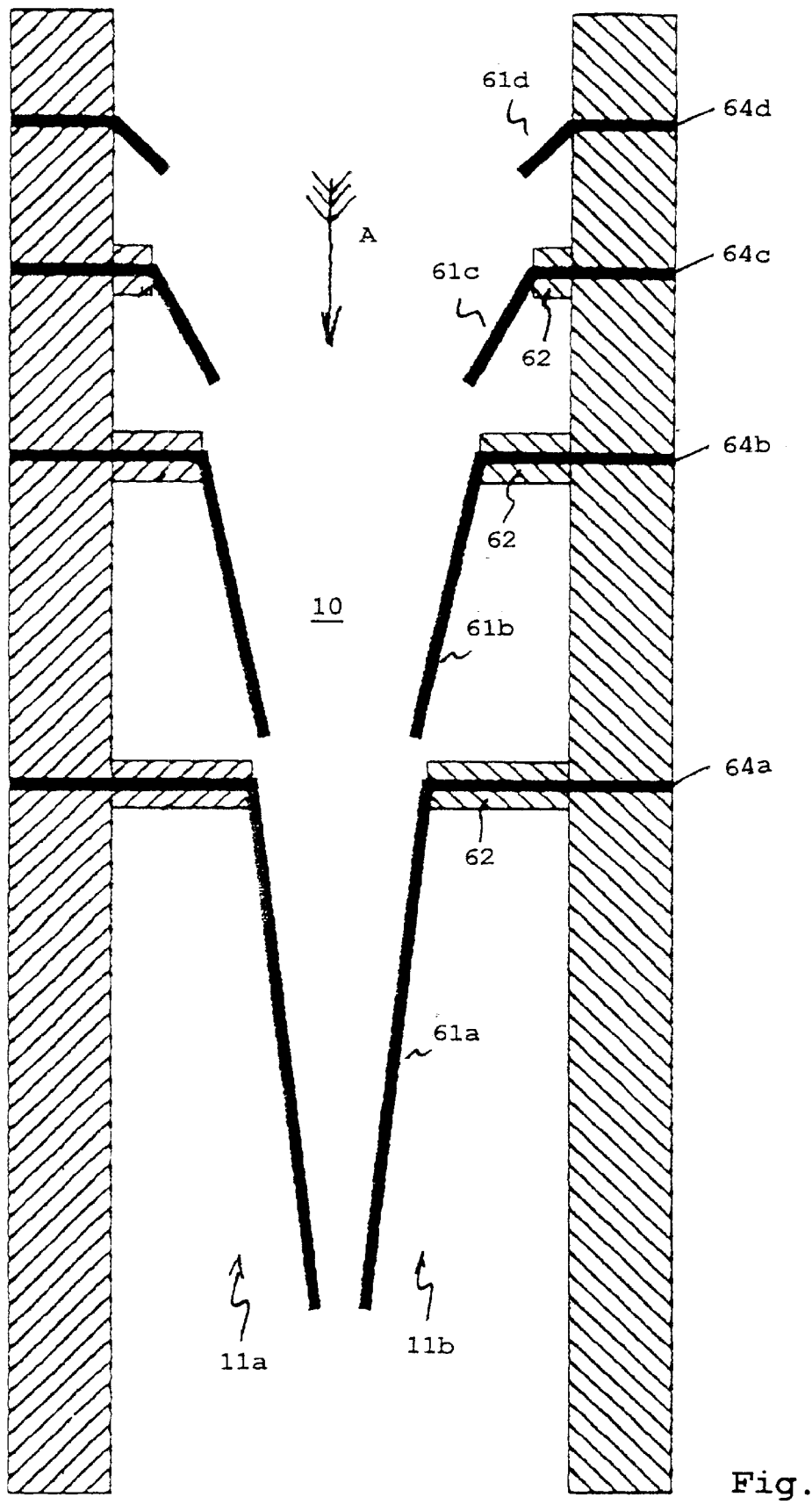
FIG. 6 is a diagrammatic top view of another particle funnel comprised of electrode segments.
Figure 7:
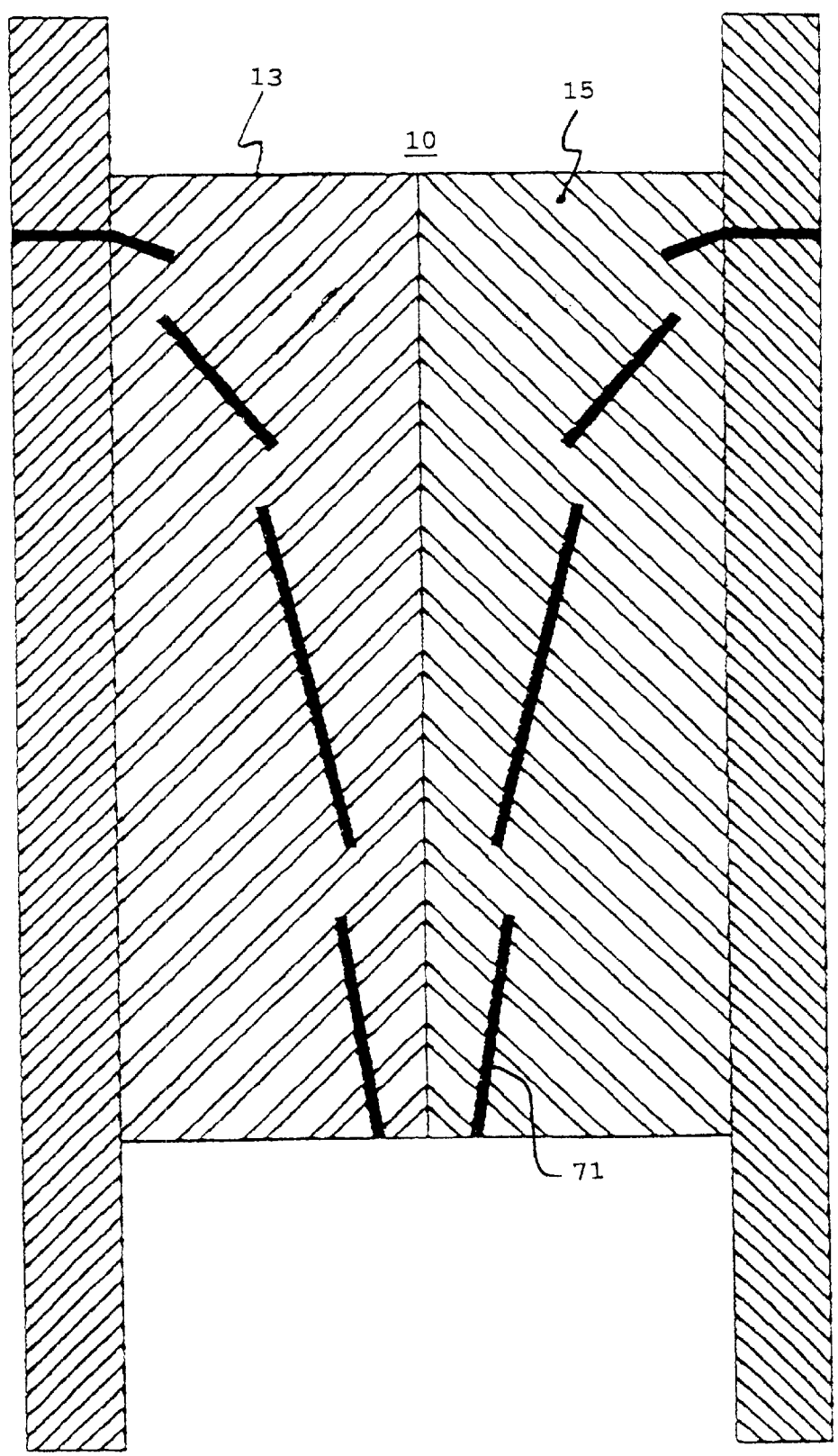
FIG. 7 is a diagrammatic top view of another particle funnel modified relative to FIG. 6.

In FIG. 1, the electrode segments form an electrode structure that will be explained in detail below drawing reference to FIGS. 5–7. The other embodiments of electrode arrangements according to the invention described below can be arranged on the bottom and/or cover surfaces of the channel 21. A suspension fluid in which particles 30 are suspended flows through the micro-channel 21 (from right to left in the figure). The object of the electrode arrangement 10 shown on FIG. 1, for example, is to guide the particles 30 from various movement paths within the channel to a central movement path according to arrow A. To this end, the microelectrodes 11, 12 are exposed to electrical potentials in such a way as to generate electrical field barriers in the channel that force the particles streaming in from the right toward the middle of the channel (arrow directions B).

Typical dimensions of the microelectrodes 11, 12 range from a width of 0.1 to several tens of micrometers (typically 5 to 10 $\mu$m), a thickness of 100 nm to several micrometers (typically 200 nm) and a length of up to several hundred micrometers. Depending on the application, the length of the electrode segments is significantly shorter as a function of their number and respective distance. The interior of the channel 21 is not limited by the electrodes processed on the top and bottom of parts 23, 24 due to the low thickness of the electrodes. Part 23 is a spacer whose structure forms the lateral channel walls.

Microelectrodes 11, 12 are actuated via high-frequency electrical signals (typically with a frequency in the MHz range and amplitude in the volt range). The respectively opposing electrodes 11a, 11b form an actuation pair, even if the electrodes lying in a plane interact in their actuation (phase, frequency, amplitude). The electrical high-frequency field generated through the channel 21, i.e., vertically to the direction of flow, acts in a polarizing manner on suspended particles 30 (which also can be living cells or viruses). At the cited frequencies and given a suitable conductivity of the suspension fluid enveloping the particles, the particles are repelled from the electrodes. As a result, the hydrodynamically open channel 21 can be on/off structured or compartmented via the electrical fields, or the movement paths of the particles can be influenced in the passive flow field. In addition, the particles can be retarded or positioned in a locally stable manner without contacting a surface, despite the permanent flow. The type and design of the electrode arrangements formed to this end is also the subject of the invention.

Embodiments of electrode arrangements according to the invention are described below, wherein only a planar electrode arrangement (or parts thereof), e.g., on the bottom of the channel, is shown in the figures for reasons of clarity.

Narrow, band-like electrodes of varying geometry are advantageous for generating electromagnetic boundaries in channel systems of microstructures, since the losses increase proportionately to the effective electrode surface. However, such narrow electrodes are very sensitive to production defects and local interruptions. A hairline fracture already causes the entire remaining portion of a band electrode to fail. In the embodiment shown on FIG. 2, narrow band electrodes are realized without the mentioned disadvantages.

The electrode arrangement 10 consists of four separately actuatable individual electrodes 11a–11d. Each individual electrode is formed by a rectangular metal coating 13, e.g., on the bottom of the channel with an accompanying control line 14. The layer thickness ranges from 50 nm to several micrometers, preferably measuring roughly 200 nm. The metal layer 13 carries a structured isolation layer 15 (shaded). The insulation layer 15 is structured in such a way that the metal layer 13 is exposed along certain recesses (black). The exposed areas form the electrode segments where the suspension fluid in the channel comes into direct contact with the electrode. If a hairline crack or other defect arises in the area of an electrode segment, the remaining metal coating ensures that all parts of the electrode segments will still be exposed to the desired electrical potentials.

Figure 2:
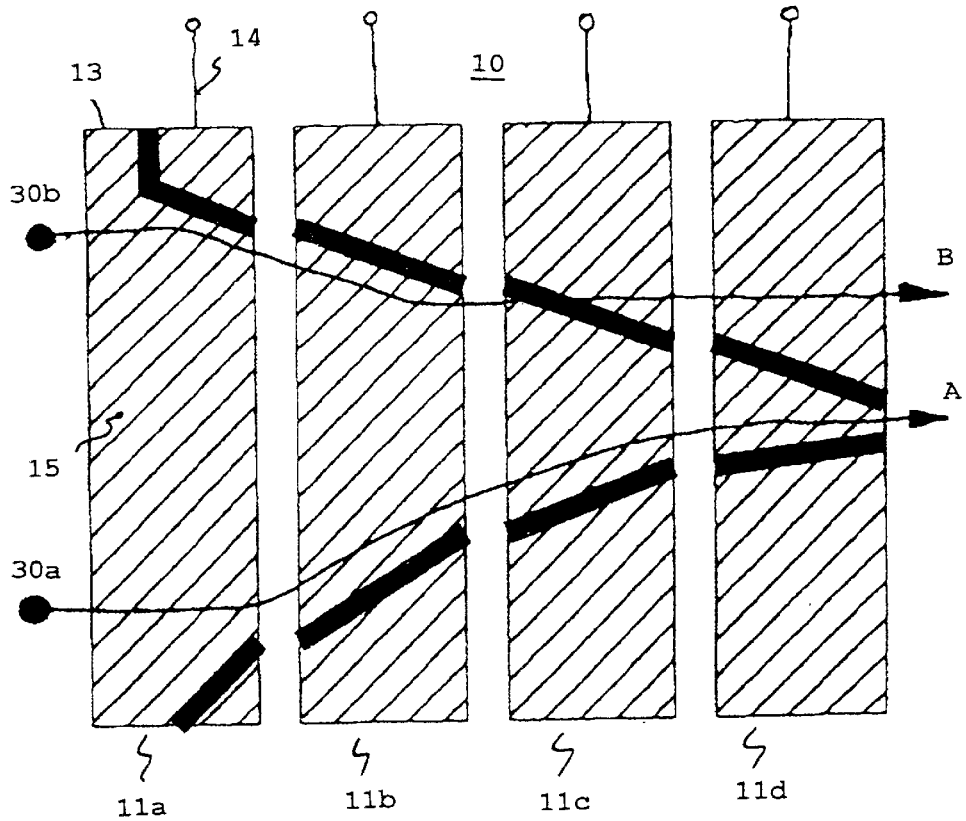
FIG. 2 is a first embodiment of the invention with band electrode segments.

In the embodiment shown on FIG. 2, the individual electrodes 11a–11d situated one next to the other are structured in such a way that two rows of electrode segments are formed. The electrode segments of one respective row, which can be straight or bent, act together to form predetermined field barriers similar to the function of a conventional microelectrode. Depending on how the individual electrodes are actuated, the following functions can be achieved here.

If the individual electrodes are actuated to form a field barrier with a funnel shape in the channel direction (particle funnel), all particles 30a, 30b are guided toward the middle of the channel, as explained above. As an alternative, however, one or more of the individual electrodes can be deactivated temporarily, so that individual particles 30a are guided toward the middle of the channel (arrow A), while other particles 30b continue to flow at a distance from the middle of the channel. In the example shown, the individual electrode 11c was deactivated for a short time just before reached by the particle 30b, thereby eliminating the field barrier in the channel in this area. As a result, the particle 30b can be conveyed further along arrow B. All individual electrodes are continuously activated for achieving the path for particle 30a.

The insulation layers in all embodiments preferably consist of biocompatible materials, e.g., oxides, $SiO_2$, $SiNO_3$, and the like), polymers, tantalum compounds or the like. Use can also be made of electrically insulating, sputtered-on materials. The thickness of the insulation layer lies in excess of 100 nm, and can measure up to several micrometers.

Figure 3:
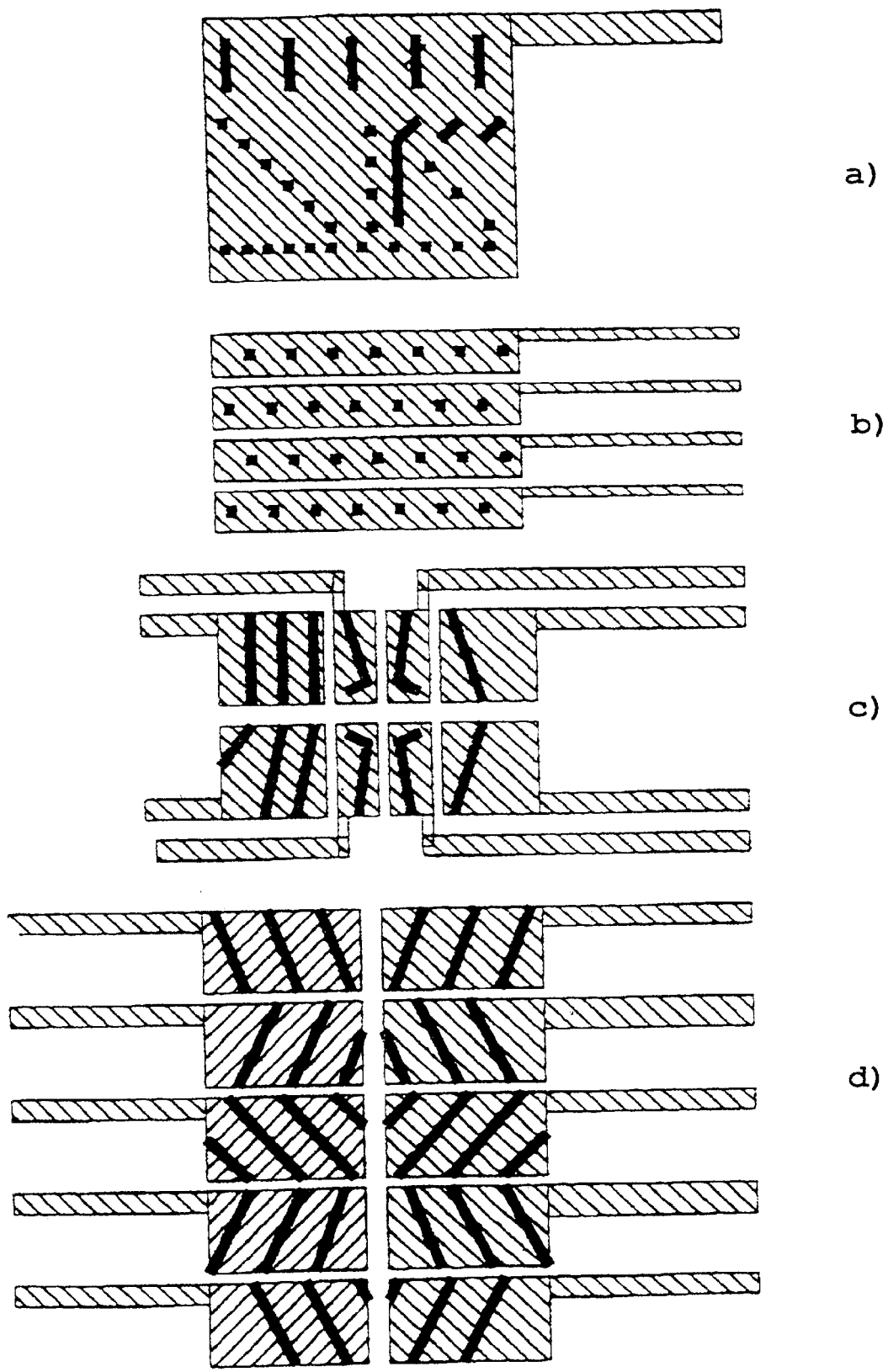
FIG. 3 are other embodiments of the invention with point or strip shaped electrode segments.

FIG. 3 shows examples of other embodiments a, b, c, d of point and strip shaped electrode segments, along with segmented electrodes similar to the electrode design described in FIG. 2. The shaded surfaces represent the metal coatings of the individual electrodes covered with an insulation layer, while the black strips or points denote the electrode segments. The electrode segments are arranged in the channel depending on application. The flow passes over the electrodes from top to bottom (or vice versa) in the respective drawing plane. The advantage of the separated electrode configuration is that the external actuation makes it possible to freely vary the effective course of the band electrodes relative to particle movement within a wide range.

Figure 4:
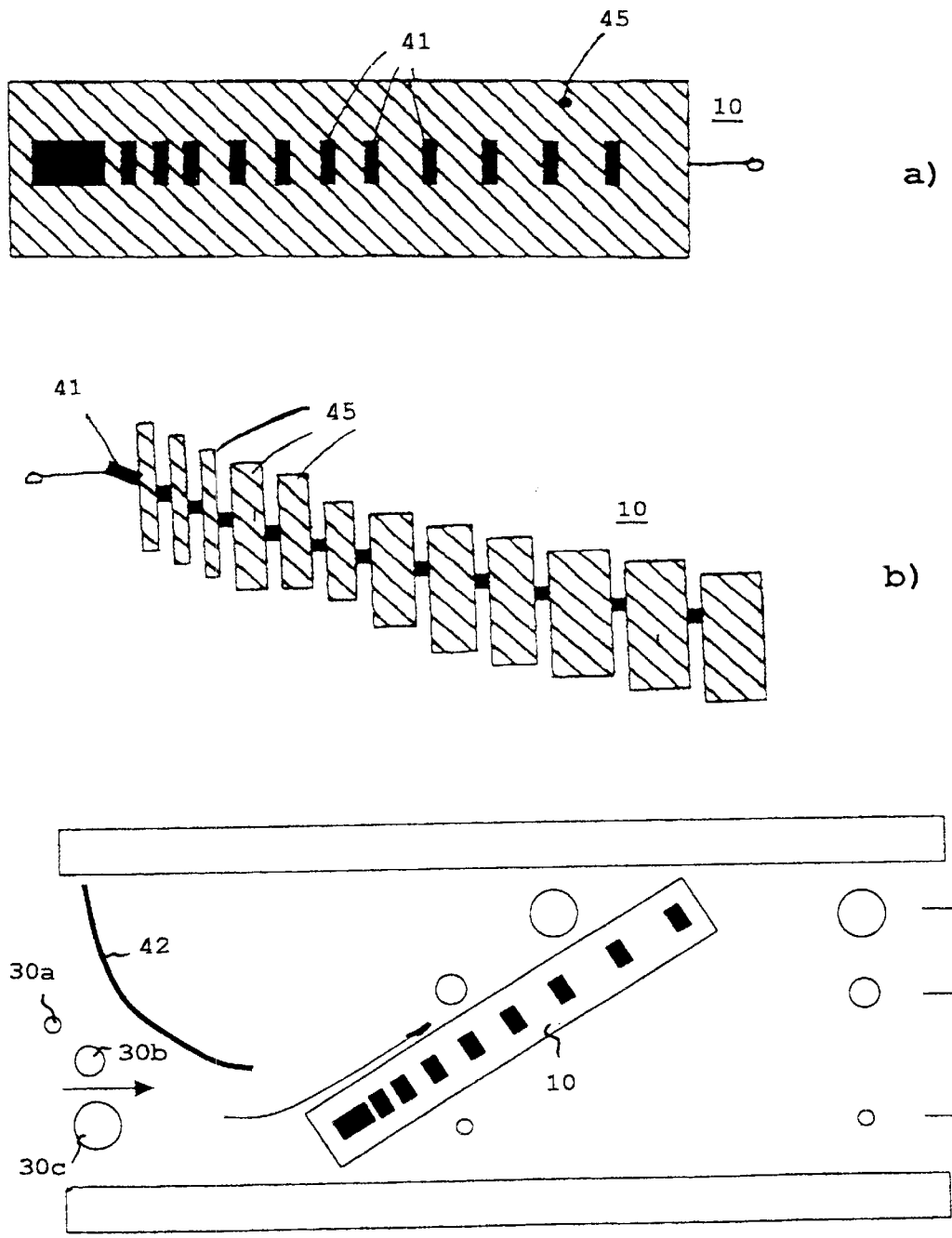
FIG. 4 are other embodiments of the invention with band shaped electrode segments for generating field gradients.

In order to sort the particles or cells (e.g., by dielectric properties or size), the field strength must be varied over the length of an electrode band. Two possible configurations are shown on FIGS. 4a, 4b. In configuration a, the distances between the recesses or electrode segments 41 in the insulation layer 45 generates a field gradient. According to configuration b, this can be achieved by applying insulation surfaces 45 of varying width on a band electrode.

The electrode arrangements 10 according to FIGS. 4a, 4b are arranged in the microsystem in such a way that the field gradient has a specific orientation relative to the direction of flow in the channel. For example, if a field gradient is formed at an inclination to the longitudinal direction of the channel, this means that the arriving particles strike a field barrier with an amplitude variable in the transverse direction of the channel. Small particles for which only slight polarization forces arise even at high amplitudes can overcome the field barrier at high amplitudes, while larger particles are deflected by the field barrier in the transverse direction of the channel until the polarization forces are small enough and the field barrier can be passed through. Therefore, one electrode arrangement according to the invention whose electrode segments form field gradients can be used for sorting particles as a function of the formation of polarization forces in the respective particles, and hence generally as a function of their size.

The principle of this type of particle sorting is illustrated on FIG. 4c. Small particles 30a can penetrate through the field barrier of the electrode arrangement 10 according to FIG. 4a at high field strengths, while larger particles 30b, 30c are only conveyed further in the channel direction at lower field strengths. The amplitudes required to this end are selected as a function of application depending on the arising flow and polarization forces. This can be done using the known control principles from microsystems technology, in particular from the manipulation of particles based on negative dielectrophoresis. The electrode 42 is used to supply the particles at the beginning of the field gradient.

Figure 5:
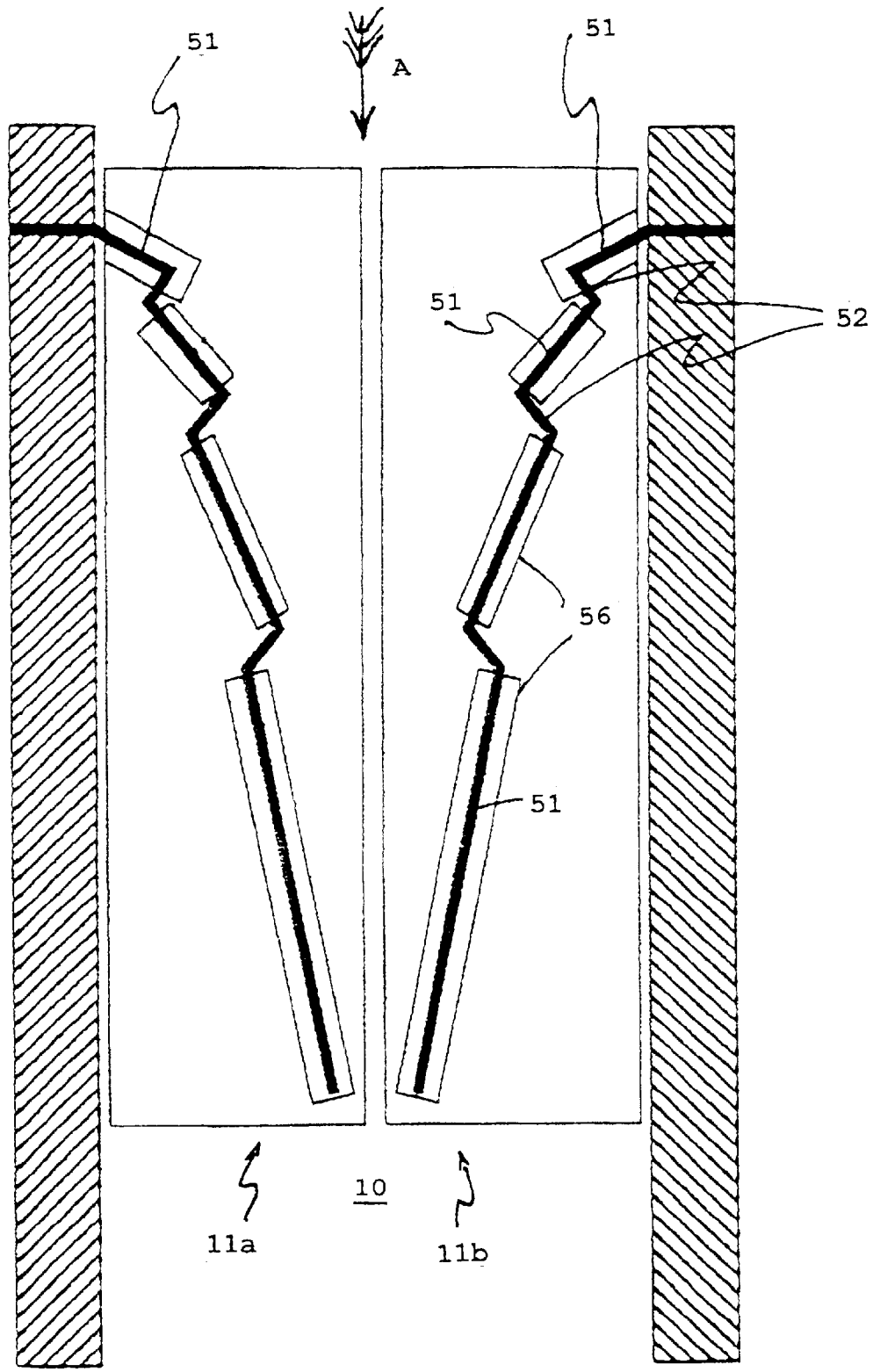
FIG. 5 is a diagrammatic top view of a micro-channel with band electrode segments to form a particle funnel.

The covering technique shown on FIG. 2 for manufacturing band electrodes can also be used for their optimization according to FIG. 5. FIG. 5 shows a modification of an electrode arrangement 10 for forming a funnel-shaped field barrier. The electrode arrangement 10 consists of two individual electrodes 11a, 11b, which each are shaped like bent electrode bands. Each individual electrode 11a, 11b is covered by an insulation layer 55 with recesses 56. The recesses 56 expose predetermined sections of the individual electrodes 11a and 11b that form the electrode segments 51. The parts 52 of the individual electrodes 11a and 11b are not electrically active due to the covering insulation layer.

The electrode bands of the individual electrodes are angled in such a way that an electrode section leading toward the middle of the channel and corresponding to the electrode segments 51 is always bordered by an electrode section facing away from the middle of the channel and corresponding to the covered feedback loops 52. This arrangement enables a smooth interaction between the electrode segments, which are geometrically separated from each other, but form overlapping field barriers in the direction of flow (see arrow A).

Another electrode arrangement will be described based on the example of the particle funnel according to FIG. 6. In media with a high atmospheric humidity, those used for animal and human cell cultures (or in sea water), losses on a band line (band electrode) can be so high that distinctly lower or even no field effects arise at their end relative to the particle covering. Under these conditions, it makes sense to divide the electrodes 11a, 11b into electrode segments 61a to d, and provide various feeds on the control lines 64a to d. The channel progression angles (arrow A) are adjusted to the flow profile in the channel. Feeding parts 62 of the electrode arrangement 10 are best insulated.

As an alternative to the configuration shown on FIG. 5, the individual electrodes can each be formed by planar metal layers based on the principle explained on FIG. 2. The electrodes can also be formed by a shared metal layer 13, which carries a shared insulation layer 15 with recesses corresponding to the desired electrode segments 71 (see FIG. 7).

In the following, a preferred embodiment of the invention will be described with reference to FIGS. 8 to 10, in which the electrode arrangement 10 consists of a high number of point shaped electrode segments 81 arranged in a matrix, which can all be individually actuated.

Figure 8:
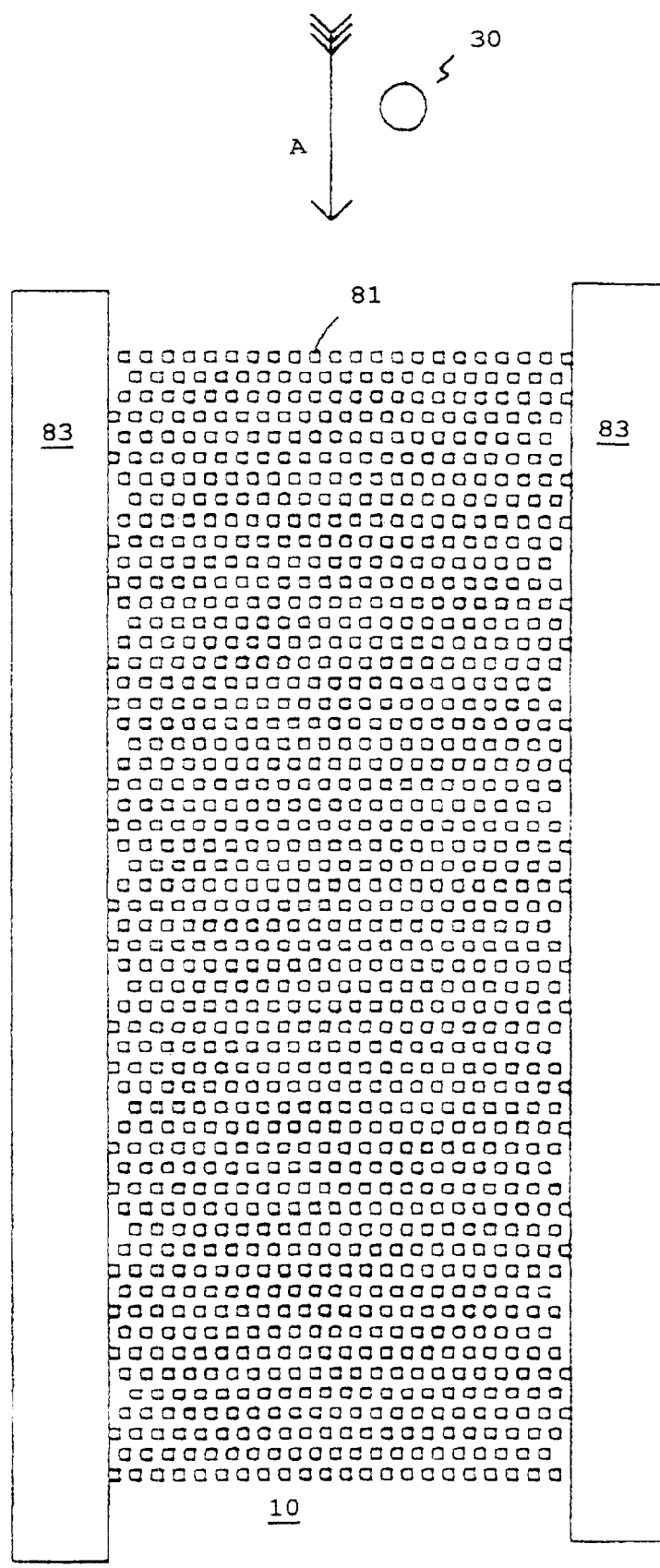
FIG. 8 is a diagrammatic top view of an electrode array according to the invention.

FIG. 8 shows the arrangement of electrode segments 81 on the bottom and/or cover surface of the channel. The electrode arrangement preferably extends over the entire channel width between the spacers 83, which form the lateral channel walls. One or more particles 30 flow in the direction of the arrow (arrow A) over the electrode arrangement 10, for example. The electrode segments 81 can be used to achieve any effects for particle deflection, in particular as were depicted on FIGS. 1 to 7, in a programmable manner via the individually actuatable point or square or rectangular electrode segments in an arrayed configuration, if the distances between the electrode segments 81 are smaller than the particles to be manipulated 30. A corresponding electrode arrangement is preferably situated on the top side of the channel, so that electrical high-frequency fields can arise from the top of the channel to the bottom of the channel. FIGS. 9 and 10 show examples for a possible actuation.

Figure 9:
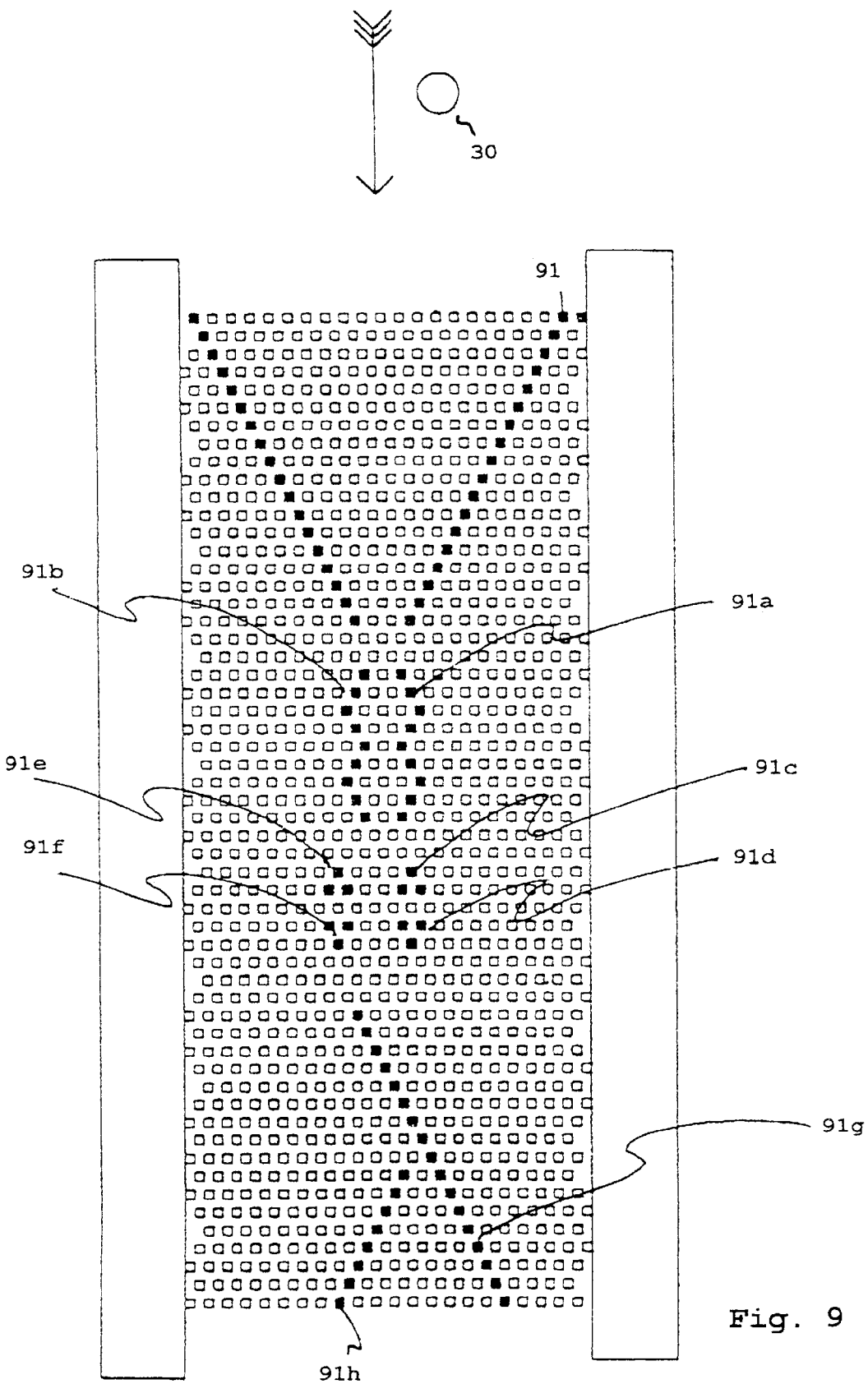
FIG. 9 is an illustration of an actuation example for an electrode array according to FIG. 7.

FIG. 9 shows as an example how an electrode array of the kind described on FIG. 8 can be actuated. The light electrode segments are not actuated. The black electrode segments 91, 91a–h are actuated with an alternating voltage (e.g., between 1 and 500 MHz). The electrode segments lying in the top plane of the channel (not shown here) are also actuated at the corresponding positions. The actuation of electrode segments will be listed in table form below as an example. In this case, the unmarked numbers denote groups of electrode segments in the lower plane, while numbers marked (') relate to the upper channel plane:

| Electrodes | Phase position |
| --- | --- |
| 91 | 0° |
| 91' | 180° |
| 91a | 0° |
| 91a' | 180° |
| 91b | 0° |
| 91b' | 180° |
| 91c | 0° |
| 91c' | 180° |
| 91d | 90° |
| 91d' | 270° |
| 91e' | 180° |
| 91e' | 0° |
| 91f | 270° |
| 91f' | 90° |
| 91g | 0° |
| 91g' | 180° |
| 91h | 0° |
| 91h' | 180° |

System function can be described as follows. The particles 30 are made to stream into the channel along the arrow. When the electrode rows 91, 91a, 91b are actuated, a field barrier comes about that focuses the particles in the central area of the flow. The particles are spaced apart from each other via electrode rows 91a, 91b. Electrode groups 91c–91f form a quadrupole, which corresponds to 91c'–91f' on the top of the channel. This group of 8 electrodes as actuated functions as a field cage, and precisely positions the particles. If this electrode group, or at least electrode segments 91d, 91f, are deactivated, the particles that flow out thereafter can be steered to the right or left side of the channel via the optional activation of the electrode rows 91g or 91h. Therefore, this system involves a particle/cell moving and sorting module.

Figure 10:
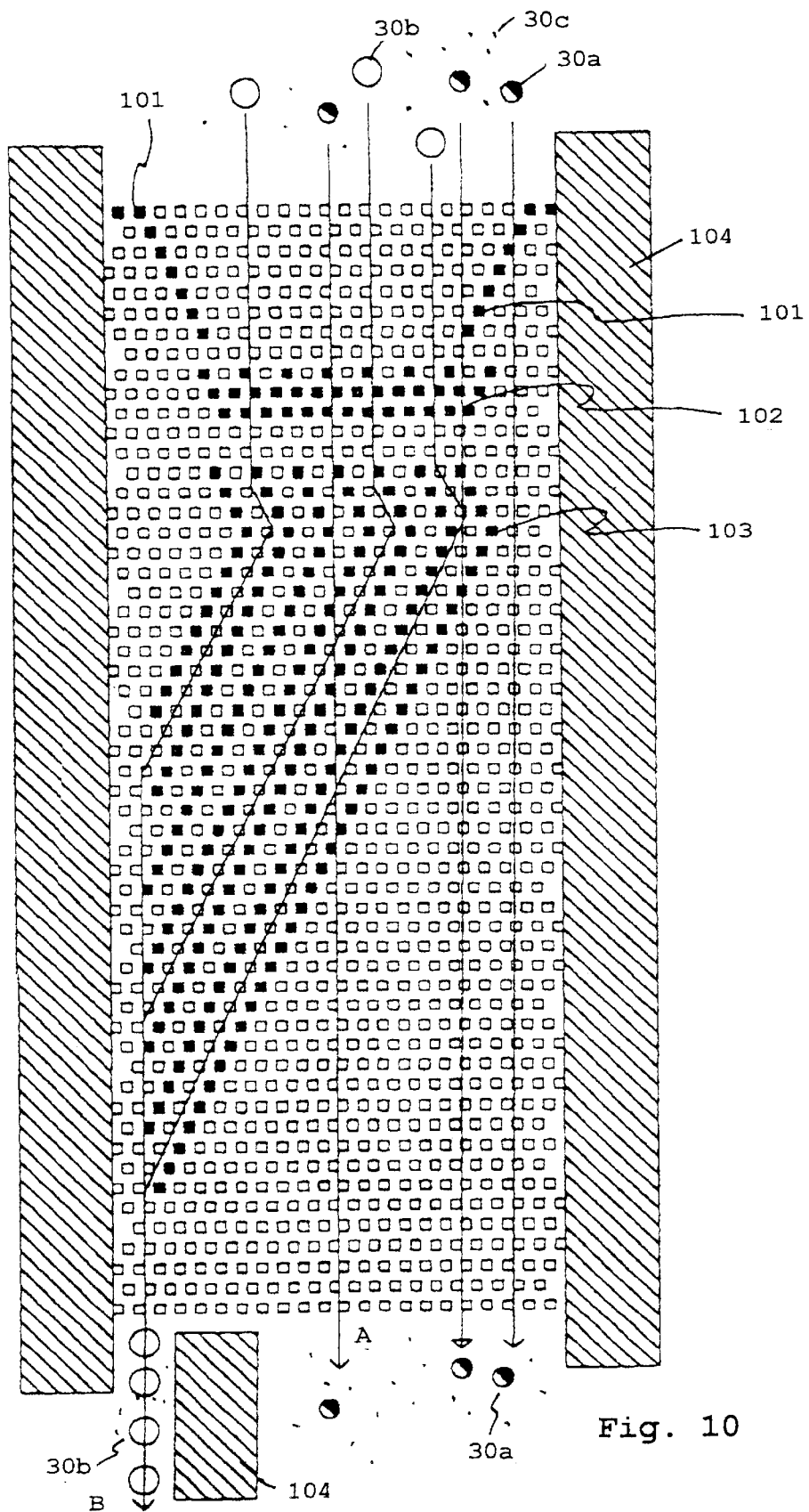
FIG. 10 is an illustration of another actuation example for an electrode array according to FIG. 7.

FIG. 10 shows an example of how actuating the electrode segments differently than on FIG. 9 can result in a new kind of function for the system. Supplied in this case is a particle mixture 30a, 30b, 30c consisting of particles that differ in size and can be dielectrophoretically influenced in various ways (30a dielectrophoretically weakly influenced particles; 30b particles larger than the distances between the electrodes and easily dielectrophoretically deflected; 30c particles distinctly smaller than the selected electrode pixel distances). The electrode groups 101a, b focus only the large particles 30b on a target 102, where they are retained, while particles 30a and 30c pass through the channel virtually uninfluenced (arrow A). If the target is deactivated and the electrode pixel rows 103 are activated, the retained particles 30b now move along the paths indicated, and can be separately intercepted (arrow B). The channel walls 104 can split the main channel into several channels.

Another application of such arrays involves the universal system, i.e., potential application of all electrode segments or pixels, which are determined and activated in an irreversible process during first use. For example, this could be done by stripping off an insulation layer, opening with an electrical pulse (duration roughly in $\mu$s to s range, voltage roughly 10 V to several 100 V), optically or based on a similar principle. The then exposed structure can now only be expanded, but not reduced. The latter can only be accomplished via the selective application of new insulations. This could conceivably be done through oxidation. One preferred means for liberating electrode pixels lying opposite each other in the channel from an insulation layer involves a dielectric breakdown through actuation of both electrodes with short electrical pulses.

Photoelectric effects can be used to achieve a reversible variant of such activations of point electrodes. Suitable semiconductors make it possible to distinctly change their conductivity via illumination. In this way, the desired electrode pattern can be activated through illumination via a mask on one or both sides of the channel.

Figure 11:
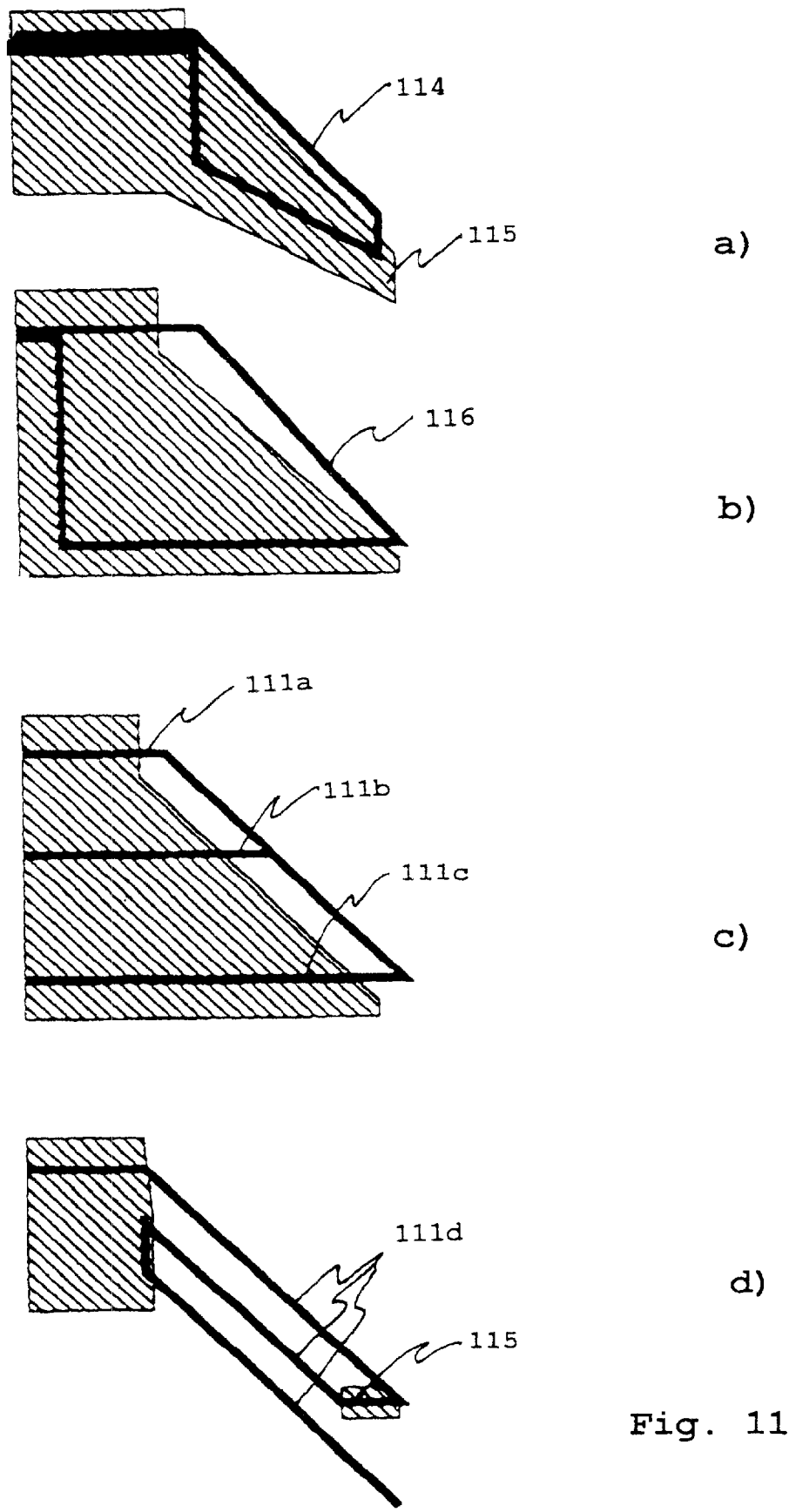
FIG. 11 are additional embodiments of electrode segments according to the invention with loops or multiple feeds.

Another important criterion for optimizing band electrodes can involve their insusceptibility to an interruption. To maintain function nonetheless, loops and multiple feeds make sense. To keep losses low, these parts of the electrodes can be electrically separated relative to the overlying suspension by means of an insulation layer. FIGS. 11a) to d) summarize several possible configurations. 114 is a ring electrode with a very small loop and an insulation layer 115. Configuration b) involves a more expansive loop 116, also with partial insulation. A microelectrode multiple feed 111a to 111c is shown on c). The feeds can either be actuated permanently, or if desired upon the failure of a lead wire.

A multiply folded band electrode 111d with partial insulation 115 is shown on configuration d). If the front part (near the feed) happens to fail, the function is still taken over by one of the other parts. The shown electrode types can be logically combined in their configurations.

Figure 12:
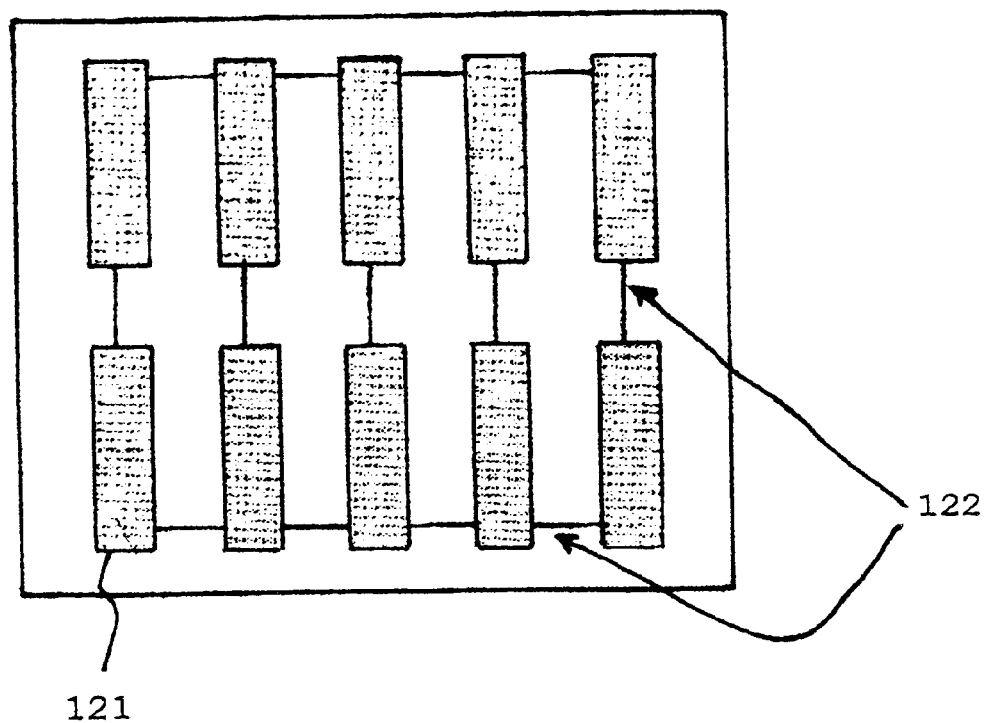
FIG. 12 is another embodiment of a programmable electrode arrangement.

FIG. 12 shows an electrode arrangement that can be programmed by electrical pulses. The ten rectangular electrodes 121 are electrically interconnected via the connection webs 122. These connection webs can be disrupted by a current pulse between two adjacent electrodes. This makes it possible to determine the interconnection between the electrodes via current pulses.

According to an embodiment of the invention, a procedure for manipulating particles in fluidic microsystems, in particular for moving particles in microsystems along predetermined paths, at least sections of which run along a straight line, and devices for implementing such a procedure are described, in particular a fluidic microsystem, in which synthetic or biological particles are manipulated in a suspension fluid, and applications of such a microsystem.

Fluidic microsystems with structures (e.g. channels) through which liquid flows, in which microelectrodes for influencing particles, (e.g. biological cells) through high-frequency fields on the basis of negative or positive dielectrophoresis are affixed to the channels through which liquid flows, have for example been described by G. Fuhr et al in "Naturwissenschaften", vol. 81, 1994, p. 528 ff.

Usually, a liquid flows through fluidic microsystems so as to move particles along. The microelectrodes attached to both the top and bottom of the longitudinal sides of the channel, result in compartimentation of the channel with high-frequency electrical fields by means of which the suspended particles can be deflected as desired, e.g. via branching out into adjacent channels or other structural elements. Above all the inflow of particles at one end of the channel and the setting of the flow speeds which as a rule are slow (some µl/h) are associated with difficulties which with increasing miniaturisation impose increasingly severe limitations.

A general disadvantage of conventional fluidic microsystems is due to the fact that directional and adjustable particle movement requires a solution flow whose control (e.g. flow speed) causes considerable problems.

From the publication by M. J. Madou et al. in "SPIE", volume 3259, 1998, p. 80 ff, a centrifugal flow-through system is known in which flows of liquid in a microsystem are not regulated with conventional pumps and valves, but instead under the influence of centrifugal forces. To this effect the microsystem is in a disc-like carrier in the shape of a CD-ROM disc. Analogous to the operation of CD storage media, the carrier is intended to be spun at high speed (ranging from 100 to 10,000 revolutions per minute). The liquids in the microsystem move radially outward under the influence of the centrifugal forces. Simultaneously to this liquid movement, certain biochemical reactions take place in the microsystem. It is also intended that the movement of liquid be utilized for conveying particles, as is the case in a conventional pumped flow of liquid.

The centrifugal technology according to M. J. Madou et al is associated with the following disadvantages. Both the achievement of sufficient movement of fluid and the achievement of conveyance of particles, which as far as is possible is free from any obstructions, in the liquid in the disk-shaped flat rotor, necessitates the above-mentioned high revolutions of the carrier. This results in a limitation of the conventional centrifugal force flow-through system to particular basic functions of traditional centrifuging or to achieving biochemical reactions. The above-mentioned microelectrode technique for generating high-frequency electrical fields in the microstructures cannot be applied. There is a further disadvantage relating to particle sorting and particle counting achieved with conventional centrifugal techniques. Such sorting and counting is possible only if the size of microchannels created corresponds to the size of the particles to be processed. Therefore, any given microsystem is always restricted to a particular particle size. In addition, when handling biological particles (cells, cell components) interactions quickly occur between the particles and the channel wall, causing blockages of the channel.

Furthermore, centrifuge systems are generally known in which the sample material in the centrifuge is not only subjected to centrifugal forces but in addition also to magnetic or electrical forces so as to achieve specific separation effects depending on the relationship between centrifugal forces and additional forces. These centrifuge systems cannot however be used to manipulate biological objects. Biological objects (e.g. cells) are handled in relatively highly conductive solutions or suspensions (conductivity ranges from approx. 0.5 to 3 Siemens/m). In the case of conventional centrifuge systems with relatively large electrode surfaces, such conductivity would result in undesirable heating-up phenomena. Conventional centrifuge systems are therefore limited to a conductivity of approx. 0.1 Siemens/m.

The aim of the inventive aspect described here is to provide an improved method for manipulating particles in fluidic microsystems, which method overcomes the disadvantages of traditional microsystems and provides an extended application range. Furthermore it is the object of the invention to provide an improved fluidic microsystem with directional particle movement which can be adjusted simply and with high accuracy. It is also the object of the invention to provide applications for such an improved microsystem.

A first important aspect consists of moving from the traditional centrifugal flow-through system with moved liquids, to a method where in a fluidic microsystem under the influence of centrifugal forces, only the particles to be manipulated are moved, with essentially no liquid flows or movements occurring in the microsystem. To this effect a number of measures are realised which in particular comprise the use of a fluidic microsystem closed off at least on one side, the provision of such a microsystem on an oscillatory rotor centrifuge, and operation of this centrifuge at a predetermined rotational speed at which the particles in the microsystem move as desired.

The method according to the invention allows centrifugal action at low speeds. Due to the use of an oscillatory rotor system where the rotor as the carrier of the microsystem is vertically aligned (at standstill or low speed), moving to a horizontal alignment (at high speeds), as the speed decreases, gravity increasingly influences the movement of the particles in the microsystem. According to a further aspect of the invention a particle movement in microsystems which are closed off on at least one side is also described, which when at a standstill is vertically aligned relative to the microsystem. Particle movement takes place as sedimentation under the influence of gravity.

According to the invention, in particular those types of microsystems which comprise microelectrode devices for dielectrophoretic influencing of particle movement, are combined with the principle of centrifuging. As a result of the centrifugal forces, the suspended particles move through the microchannels or other microstructures in a microsystem in which they (without being able to exit) are for example separated, brought to a predetermined position, fused, sorted or permeated under the influence of electrical polarisation forces.

The invention provides an important advantage in that for the first time in the case of microsystems with a complex structure, involving dielectrophoretic particle influencing, there is no need to use pumps or valves which are difficult to control and subject to malfunction, without this resulting in any limitation in the functionality of the microsystem. There are no limitations in relation to the dimensions of the channel cross sections. There is an option of rotating the microsystem simultaneously together with the associated control electronics. Interactions between particles (in particular biological particles) and wall areas of the microsystem can easily be prevented. Conversely, with respective structuring, such interactions can be achieved in a predetermined way for investigating binding procedures.

The invention provides an important advantage in that all particles can be subjected to the same extent to centrifugal forces, and can move corresponding to a reference direction along predetermined channels, and separation e.g. in various sub-channels or reservoirs is exclusively achieved via deflection forces which act in a particle-specific way, independent of the centrifugal forces. The direction of the deflection forces differs from the reference direction, with the angular difference being preferably less than 90°. Only the particle speed is set via the centrifugal force. After separation, the additional forces can be switched off without the particles mixing again. It is an unexpected and important characteristic that through the use of a swinging rotor centrifuge, the contact between particles and sample chamber walls can be prevented. This is of importance especially in the case of biological objects.

Figure 13:
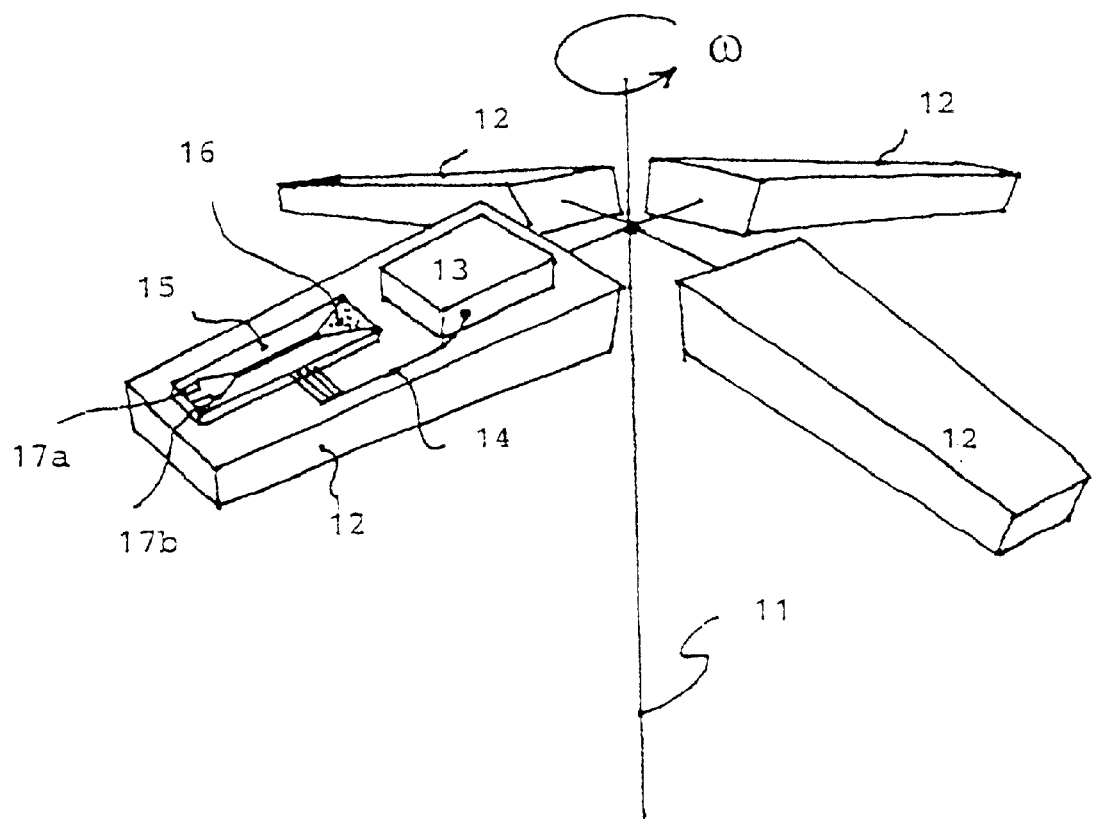
FIGS. 13 to 15 are additional embodiments of the invention based on a microsystem with centrifugally and/or gravitationally induced particle movement.
Figure 14:
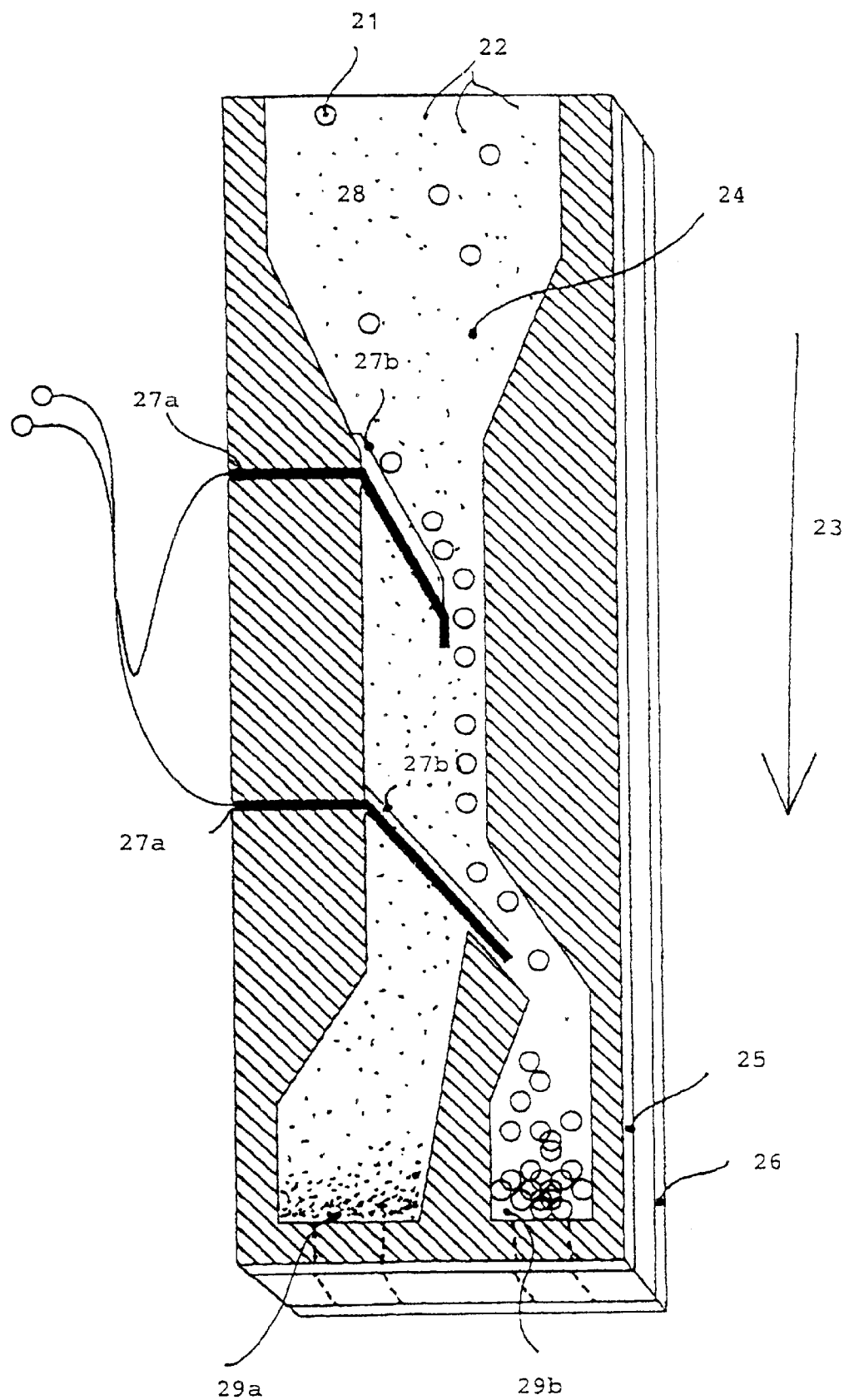
Figure 15:
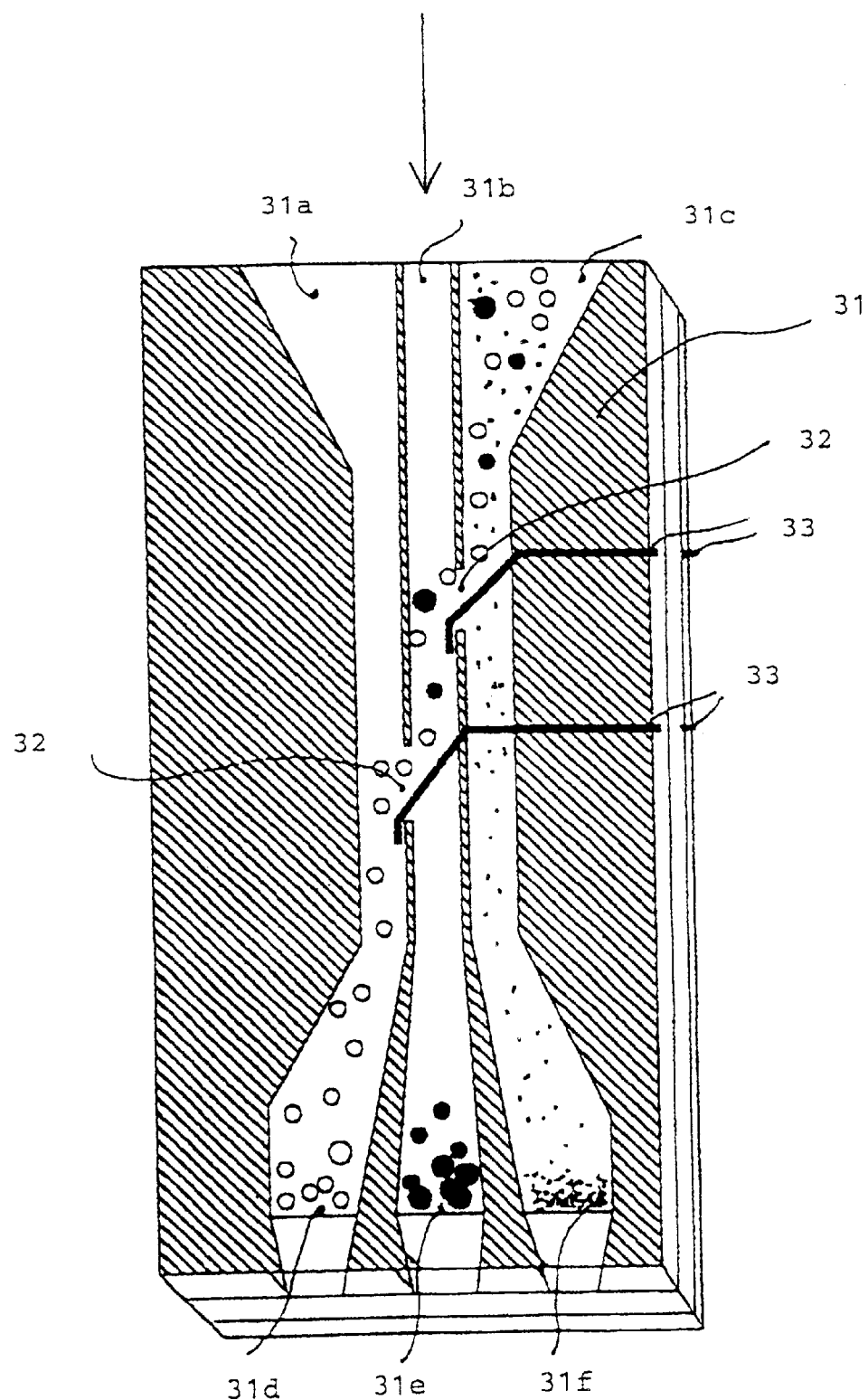

FIGS. 13 to 15 show a diagrammatic perspective view of a design according to the invention of a centrifuge with a microsystem; a diagrammatic top view of a microsystem according to the invention configured for particle separation; and a diagrammatic top view of a programmable loading microsystem according to a further embodiment of the invention.

The embodiments of the invention described in this part refer to a combination of a microsystem comprising a microelectrode arrangement for carrying out negative or positive dielectrophoresis (dielectrophoretic microsystem) comprising a swinging rotor centrifuge. Both the dielectrophoretic microsystem (apart from the channel structures capable of being closed off at least on one side) and the swinging rotor centrifuge are known per se. Consequently there is no need to discuss their technical details here. It must be emphasised that in this document the term "swinging rotor centrifuge" is to be interpreted in the widest sense in that any centrifuge comprising at least one rotor which can be hinged upright depending on the speed, is included, which rotor itself forms the microsystem and the associated control system; into which rotor the microsystem and the associated control are integrated; or onto which rotor the microsystem and the respective control system are superimposed.

The particles manipulated according to the invention can comprise synthetic particles or biological objects. The synthetic particles are for example membrane-surrounded formations such as liposomes or vesicles or so-called beads or also macromolecules. The biological objects comprise for example biological cells or components of such cells (e.g. cell organelles), bacteria or viruses. The particles can also be aggregates or agglomerations of such particles and/or objects. The invention is preferably implemented using cell-physiologically relevant or medically relevant fluids with conductivities below 5 Siemens/m.

FIG. 13 is a diagrammatic overview of a device according to the invention for illustrating the affixation of a dielectrophoretic system to a centrifuge device.

A usual or application-dependent modified rotor of a centrifuge with axis of rotation 11 comprises four receptacles 12 into which the following are inserted so as to fit snugly and to tolerate the speeds applied: a microsystem 15 and control electronics 13 for controlling the microsystem with high-frequency alternating signals of different phase positions and amplitudes. The control electronics are connected to the microsystem 15 via cable 14, connector or otherwise. Preferably, the energy supply to the control device is via an electrical connection (rotation contact) with the stationary laboratory system. The microsystem comprises an input depot 16, the size of which can vary depending on the application, said depot 16 prior to centrifugation being filled with a particle suspension or cell suspension. From the input depot 16, a channel structure (details of which are provided below), extends to the collecting zones 17a, 17b which form an end of the microsystem 15 which end is closed at least during centrifuging. This means that the end of the microsystem can either be permanently closed off, or during standstill of the device can be opened by way of respective connection elements, and can be connected to predetermined additional systems for transferring the samples. The microsystem 15 is arranged on the retainer 12 such that during operation of the centrifuge (rotor turning around the axis of rotation 11 at a rotation frequency of ω), the centrifugal forces acting on the microsystem 15 and the particles located in said microsystem, are directed in the reference direction from the input depot 18 towards the collecting zones 17a, 17b. The retainers 12 are attached to the rotor (not shown) so as to be hingeable. With the centrifuge at a standstill, the retainers 12 are essentially aligned vertically or at a shallow angle in relation to the axis of rotation. During operation of the centrifuge, depending on the speed, the retainers 12 come up to a larger angle until they are aligned horizontally, i.e. perpendicular to the axis of rotation 11. Under the influence of gravity (with the centrifuge at a standstill) or the centrifugal forces, the particles flow through the electronically controlled microchannel system and congregate in the collection zones (e.g. at the closed end of the part of the microsystem pointing away from the rotor axis).

During this passage, the particles are treated according to predetermined programs (see below). Since the particles carry out various movements and assume various end positions depending on their density, the present invention combines the advantage of centrifugal separation and centrifugal movement with the possibilities of preprogrammable dielectrophoresis. Normally, negative dielectrophoresis of the particles is used; in exceptional cases also positive dielectrophoresis. Control of particle movement via rotational speed (ω) of the rotor 11 is a further advantage provided by the invention. Since in this case it is also possible to pass through programmable variations, a second complex of determinable parameters during particle manipulation is provided.

The centrifuge device comprises a rotational speed control (not shown) which provides a reproducible and precise speed adjustment in particular at low speeds. The rotational speed is selected application-specifically, depending on the desired speed of the particles to be manipulated and depending on the actual design of the centrifuge. For biological particles (e.g. cells), the interesting particle speeds are below approx. 500 $\mu$m/s (preferably ranging from 50 to 100 $\mu$m/s); for synthetic particles (e.g. latex beads) the speeds are higher (e.g. some m/s). The rotational speed of the centrifuge is selected according to the interrelationship between rotary speed and centrifugal force, depending on the size or density of the particles. The following information refers to a spacing of the microsystem from the rotor axis, ranging from 1 to 10 cm. For particle diameters ranging from 50 to 600 nm (e.g. viruses), rotational speeds can range from 1 to 1,000 rpm. In the case of particles with a diameter of approx. 5 $\mu$m, rotational speeds up to 100 rpm are preferred, but higher speeds can be set. In the case of particularly small particles, e.g. macromolecules, still higher rotational speeds can be realised. For biological cells, at a distance between the microsystem and the axis of rotation 11 of approx. 5 to 10 cm, speeds ranging from a few revolutions per minute to several hundred (e.g. 600) revolutions per minute result; preferably below 100 rpm. Achievable centrifugal forces are in the region of pN to nN. The centrifuge is however also designed for higher speeds which can be set in particular for small particles or for cleaning or rinsing purposes. These increased speeds can range up to the speeds of conventional laboratory centrifuges.

The rotational speed of the centrifuge is also selected depending on the dielectrophoretic forces acting on the particles in the microsystem. The dielectrophoretic forces as polarisation forces depend on the type and size of the particles. The speed is preferably selected so that the centrifugal forces acting on the particles are less than, or equal to, the dielectrophoretic forces. If these are not known, the speed can also be selected in relation to the following criterion. The particles must move slowly enough along the channel structure, so that sufficient time remains for dielectrophoretic deflection when they pass the microelectrode equipment. The effectiveness or ineffectiveness of dielectrophoretic deflection depending on rotational speed, can be acquired optically or electrically using suitable sensors.

FIG. 14 diagrammatically shows a microsystem for separating a particle mixture comprising larger particles 21 (e.g. cells) and smaller particles 22, present in a suspension. The centrifugal forces act in the direction of the arrow 23 (reference direction). Typical dimensions of the channel structure 24 are as follows:

Width: some 10 µm to some mm
(typically: 200–400 µm)
Length: some mm to some cm
(typically: 20–50 mm)
Height: some µm to some 100 µm
(typically: 50 µm)

On the top 25 and on the bottom 26 of the channel 24, microelectrodes 27a, 27b are arranged opposite each other. When these microelectrodes are selected with an alternative voltage (as a rule a frequency in the MHz range and an amplitude of some volts), they create field barriers across the channel. By way of negative dielectrophoresis (under certain circumstances also positive dielectrophoresis), said field barriers deflect the particles (the large particles in the case shown here).

The channel structure 24 extends from the input depot 28 to the closed ends 29a, 29b of the channel into which said channel, which is straight in the middle section, branches. A first pair of the microelectrodes 27a, 27b is arranged directly at the end of the input depot 28, which end faces the channel, so as to form a field barrier which protrudes transversely into the channel and which has the task of forcing the large particles 21 into the channel 24 shown on the right in top view. A second pair of the microelectrodes 27a, 27b is arranged directly in front of the branching-off to the ends 29a, 29b of the channel; it forms a field barrier which extends transversely across the width of the channel up to the branching-off leading to the channel end 29b, said field barrier being provided to guide the large particles 21 to this end of the channel.

A manipulation process according to the invention which in this example is directed to separate the particles, comprises the following steps.

Before centrifugation, the microsystem is filled with a suitable liquid. The microsystem has already been installed in a retainer 12 of the centrifuge (see FIG. 13). But installation can also take place after filling of the microsystem. Shortly before start of centrifugation, the electrodes 27a, 27b are controlled and in the input depot 28, the suspension of the particles to be separated is added, e.g. by means of a pipetting apparatus. At first, the centrifuge is in idle position, i.e. the microsystem is aligned so as to be vertical or at a slight inclination to vertical. Gravity acting on the particles results in the particles descending at different speeds to the channel structure (sedimentation), with the speed of descent depending on the density of the particles. Depending on the desired particle speed, further movement of the particles towards the ends of the channels is exclusively under the influence of gravity or under the combined influence of gravity and centrifugal forces. Centrifugation can thus be understood to be sedimentation under the influence of an artificially increased acceleration of fall. The moving particles are separated according to their size, by the electrical field of the first pair of microelectrodes.

FIG. 14 shows the conditions during sedimentation or centrifugation. As a result of the centrifugal forces being precisely adjustable via the rotational speed, the particles move to the lower part of the microsystem. According to the usual centrifugation principles, the particles with the highest density sediment first. Since the electrical field barrier in the channel moves the particles 21 to the right, while particles 22 are not influenced by this process, separation of the two particle types into the ends of the channels 29a, 29b takes place. In addition, the particles in each of the ends of the channels are arranged according to their density as is the case in conventional centrifugation. The microsystem shown can be regarded as a basic form of a device according to the invention. Depending on the application, this basic form can be enlarged, expanded or combined with further microstructures. It provides the advantage that there is no solution flow, while particle movement is nevertheless directed and adjustable. Such systems can also generate movement in the opposite direction if the particles are buoyant.

Starting with the base form shown, a microsystem according to the invention can be extended as desired, as is known per se from dielectrophoretic microsystems. Accordingly, the channel structure may in particular comprise several individual channels, interconnected by means of branch channels. Channels can be straight or curved. Curved channel shapes (e.g. arcs, meanders, curves, angles etc.) can in particular be used to investigate differences in binding between the particles and the channel walls.

According to a further modification, the microsystem can be attached to the retainer 12 (see FIG. 13) so as to be rotatable. During a first centrifugation process, e.g. particle separation according to FIG. 14 takes place in a first orientation of the microsystem. Subsequently, the orientation of the microsystem is changed by 180°, so that gravitational and/or centrifugal forces act in opposite direction to the direction of arrow 23. In this case the ends 29a, 29b of the channels assume the function of input depots from which further distribution of the separated particles into sub-groups or to treatment (loading with substances, electroporation and similar) can take place if suitable channel structures (additional lateral branch-channels) are present. Depending on the channel structure, changes in orientation other than the 180° reversal are possible. Furthermore it is possible to design the retainer 12 such that the microsystem is rotated during centrifugation.

FIG. 15 shows a further embodiment of the invention, namely a programmable loading-microsystem for cells or particles. In this embodiment the centrifugation channel is divided into three parts 31a, 31b, 31c. In the intermediary walls there are apertures 32 through which again electrodes 33 protrude at the top and bottom of the channel. The apertures are matched to the particle size (typically 5 to 20 times larger than the diameter). At first, each of the parts 31a to 31c of the channel is filled with various solutions which are used for chemically changing or loading the particles. After this, the particles are inserted into one part of the channel (in the example shown e.g. 31c). Through centrifugation, the particles (e.g. first the black ones, then the light ones) move to the electrodes 33 where they can automatically be conveyed via the electrical field barriers to the adjacent solution through the apertures 32.

Here too, sorting into the three channel ends 31d, 31e, 31f and at the same time arrangement of the particles according to their mass density, take place.

The microsystems are further characterised in that they may comprise apertures (inflows, through-flows, outflows) which can be closed off so that after or before centrifugation, the particles can easily be removed or inserted. Furthermore, all the microelectrode elements (holding electrodes for particles, microfield cages etc.) can be installed which are known per se for dielectrophoretic influencing of particles, and which are used in conventional microsystems which operate with flowing liquids. Based on the combined action of gravitational or centrifugal forces with dielectrophoretic forces, the method according to the invention is an electrically controlled or active centrifugation. Furthermore, combinations can be provided with the effect of optical forces (laser tweezers), magnetic forces (influence on magnetic particles), or mechanical forces in the form of ultrasonic forces.

Areas of application of the invention include in particular: cell separation/cell fractionation, cell sorting, cell loading (molecular, nano-particles, beads), cell discharge (molecular), cell permeation (so-called electroporation), cell fusion (so-called electrofusion), cell pair formation, and cell aggregate formation.

The invention is not limited to particular solution liquids or suspension liquids. It is advantageous if the viscosity of the liquid contained in the microsystem is known. If the viscosity is known, the rotational speed for setting a particular particle speed can be determined on the basis of tabular values or by means of a program algorithm. Alternatively, it is however also possible to acquire the actual speed of the particles in the microsystem during centrifugation (e.g. by using an optical sensor) and to regulate the rotational speed for setting a particular particle speed. It can be provided that in various sub-sections of the channel structures, e.g. in parallel channels which are interconnected only via an aperture, liquids of various viscosity are contained. In this case however, viscosities are preferred which ensure that diffusion of the liquids through the aperture is relatively low or negligible over the entire period of centrifugation.

If the mass density of the particles is less than that of the liquid in the microsystem, the invention can be implemented with corresponding modifications in that particles are introduced on the side of the microsystem away from the axis of rotation. They then move to the other end of the microsystem under the influence of buoyancy or by the combined effect of buoyancy and centrifugal forces.

The microsystem is designed corresponding to the channel structure and alignment of the electrodes in dependence on the particular application. As a rule, the cross-sectional dimensions of channels are significantly larger than the diameter of individual particles. Advantageously, this prevents blocking of the channels. If only particles with particularly small dimensions have to be manipulated (e.g. bacteria or viruses or cell organelles), then the channel dimensions can be reduced accordingly, e.g. to dimensions below 10 $\mu$m.

The invention is implemented with a microsystem which is closed off at least on one side. The closed end can be a closed-off end of a channel, a closed-off collection zone or a closed-off hollow space in the microsystem. With particle manipulation according to the invention, there is essentially no movement of liquid towards the closed end. In particular with implementation of collection zones or hollow spaces at the closed-off end, this means that these, like the entire microsystem, are filled with the solution or suspension for the particles at the beginning of particle manipulation.

If during manipulation of the particles, agglomerations or temporary blockages of the channel structures occur, according to the invention it is provided to temporarily increase the rotational speed of the centrifuge so as to detach the adhering particles and move them on.

What is claimed is:

1. A microsystem being adapted for the dielectrophoretic manipulation of particles in a suspension fluid in a channel and containing an electrode arrangement with at least one electrode arranged on a lateral wall of the channel, said at least one electrode having a plurality of electrode segments formed as open electrode surfaces, between which electrically insulating layers are provided on the surface of the microsystem facing the channel, wherein the electrode segments are adapted to generate at least one field gradient for influencing the movement paths of the particles in the channel, wherein said at least one electrode has at least one metal coating that carries an insulation layer with recesses through which said at least one metal coating is exposed toward the channel thereby forming the electrode segments of said at least one electrode.

2. The microsystem arrangement according to claim 1, in which the electrode segments of said at least one electrode are electrically interconnected.

3. The microsystem according to claim 1, in which the recesses are adapted point or line shaped to generate square or band shaped electrode segments.

4. The microsystem according to claim 1, in which the electrode segments of said at least one electrode are electrically separated from each other and individually actuatable.

5. The microsystem according to claim 1, in which the electrode segments of said at least one electrode are arranged in a matrix as an electrode array.

6. The microsystem according to claim 1, in which the electrode segments of said at least one electrode are arranged in the form of straight or bent rows, which each extend along a channel wall from the edge of the channel toward its center to form a funnel-shaped field barrier.

7. Method of using an electrode arrangement according to claim 1, for the manipulation of synthetic or biological particles in microsystems based on negative or positive dielectrophoresis.

* * * * *